United States Patent
Schuster et al.

(10) Patent No.: US 6,254,903 B1
(45) Date of Patent: Jul. 3, 2001

(54) PROCESS FOR MAKING BAKED ARTICLES THAT RETAIN FRESHNESS

(75) Inventors: Erwin Schuster, Bensheim; Bruno Sproessler, Rossdorf; Juergen Hofemeister, Gatersleben, all of (DE)

(73) Assignee: Roehm GmbH, Darmstadt (DE)

( * ) Notice: Subject to any disclaimer, the term of this patent is extended or adjusted under 35 U.S.C. 154(b) by 0 days.

(21) Appl. No.: 09/308,249

(22) PCT Filed: Nov. 13, 1997

(86) PCT No.: PCT/EP97/06331

§ 371 Date: Sep. 22, 1999

§ 102(e) Date: Sep. 22, 1999

(87) PCT Pub. No.: WO98/23162

PCT Pub. Date: Jun. 4, 1998

(30) Foreign Application Priority Data

Nov. 22, 1996 (DE) .............................................. 196 48 343

(51) Int. Cl.⁷ ...................................................... A21D 8/04
(52) U.S. Cl. .................................. 426/52; 426/18; 426/28; 426/622; 426/496

(58) Field of Search .................................. 426/20, 18, 52, 426/549, 555, 496, 28, 622, 64; 435/203

(56) References Cited

U.S. PATENT DOCUMENTS 4,416,903 * 11/1983 Cole ........................................ 426/18

FOREIGN PATENT DOCUMENTS 288 395 * 3/1991 (DE) .
96/32472 * 10/1996 (WO) .

* cited by examiner

*Primary Examiner*—Keith Hendricks
(74) *Attorney, Agent, or Firm*—Oblon, Spivak, McClelland, Maier & Neustadt, P.C.

(57) ABSTRACT

The invention relates to a method for the production of baked goods from cereal products with use of enzymes, with the aim of preventing the baked goods from going stale. To this effect, a *Thermoactinomyces vulgaris* alpha amylase is added, which makes possible targeted partial hydrolysis of the starch, and in the process prevents its retrogradation to a large extent, and is simultaneously deactivated by the baking process.

8 Claims, No Drawings

PROCESS FOR MAKING BAKED ARTICLES THAT RETAIN FRESHNESS

This application is a 371 of PCT/EP97/06331, filed Nov. 13, 1997.

BACKGROUND OF THE INVENTION

1. Field of the Invention

The invention relates to a process for making baked articles from grain products using enzymes, with the objective of preventing staling of the baked articles.

2. Description of the Background

Prevention of staling or, stated positively, retention of freshness of baked articles has been a problem as long as bread has been baked. Heretofore the sales outlets for baked articles, the bakeries and even the consumers have made the best of the situation and become accustomed to the fact that rolls, for example, must be sold and eaten on the same day. Prolonging the freshness by several days would be desirable and would decisively change consumer behavior and the distribution strategy for this important basic food. In the course of the wave of innovations in food technology in recent years, enzyme technology has confronted this problem and already suggested several solutions.

The staling process is extremely complex and in no case is completely understood. Even the manifestation of the effect is multi-faceted. The following adverse phenomena are observed:

1. An increase in firmness of the crumb. The bread becomes hard.
2. The bread crust becomes leathery or rubbery.
3. Loss of bread aroma. An unpleasant odor characteristic can even develop.

The experts unanimously believe that staling of baked articles is related to retrogradation of the starch and to the associated change in water-retention capacity. Starch is an essential constituent of baked articles, and is present in dough in the form of particles coated with protein. During the baking process the starch becomes gelatinized and absorbs copious water, while the protein coagulates. Immediately after baking the starch begins to recrystallize (=retrograde) and release water. The firmness of the crumb increases, although this is still regarded as an advantage in the first four hours. The sliceability and chewing characteristics improve at first. It is assumed that the unbranched starch fraction, or the amylose, crystallizes first, followed by the branched fraction of the starch, or the amylopectin, during further storage. In the meantime the crumb becomes stiffer and in the course of time increasingly less elastic and eventually dry and hard: the bread has become stale.

In contrast, the crust loses crispness during storage. It is assumed that water is released by recrystallization, diffuses outward from the crumb and moistens the crust completely through. As a result, the crust becomes tough and leathery. Among the possible reasons for the loss of aroma of stale bread may be inclusion of the aroma substances in the starch helix.

It is undisputed that the causal key reaction for all of these staling phenomena is starch retrogradation. Suppressing or circumventing this phenomenon is the subject matter of numerous protective rights and publications.

One strategy for hindering at least partly the considerable firming of the crumb during storage has already been long known: the crumb is made in softer form from the beginning. The means of choice are emulsifiers such as lecithin, lysolethicin, diacetyltartaric acid esters or monoglyceride and diglyceride esters, which are added to the dough and produce crumb structure which is particularly soft from the beginning. It is also postulated that the monoglyceride and diglyceride esters on the one hand absorb the water released by recrystallization and on the other hand associate with the amylose, thus interfering with recrystallization thereof to the point that it can no longer proceed to completion. The use of alpha-amylase derived from fungi such as *Aspergillus oryzae* also has a similar effect. It acts upon damaged starch particles, thereby lowering the viscosity of the dough and producing fermentable sugar. As a consequence, the finished baked article has larger volume, which is consistent with softer crumb: The process of firming during aging is not as pronounced when the crumb is particularly soft.

Aside from the fact that the fresh bread is too soft, this strategy does not prevent or inadequately prevents the development of a rubbery consistency of the crumb as well as the other flaws of bread when it becomes stale.

A further strategy, specifically that of preventing retrogradation by partly enzyme-mediated hydrolysis of the two starch fractions, is therefore more promising. It is assumed that the fragments produced by hydrolysis of the starch are too short to be able to recrystallize. The fragments associate with the remaining high molecular weight starch and largely prevent recrystallization thereof as well. In the experts' view, enzyme-mediated hydrolysis of the crumb should take place if possible at the gelatinization temperature, or in other words above about 70° C. These temperatures are reached and exceeded without difficulty in the baking process. The dilemma of enzyme treatment, however, is that only partial hydrolysis is permissible: not too little and not too much. If the degree of hydrolysis is too low, the freshness will not be retained. This is the case, for example, if starch-cleaving enzymes with too low thermal stability are used, such as the above-mentioned alpha-amylase derived from fungi. Such an enzyme has already lost its activity if gelatinization begins in the course of the thermal stress during the baking process, with the result that hydrolysis of the starch is too little.

The use of alpha-amylases derived from bacteria such as *Bacillus subtilis* or *Bacillus stearothermophilus* leads to high degrees of hydrolysis. Because these are extremely thermally stable they are hardly deactivated during the baking process and even act subsequently during the cooling process. The consequence is excessive breakdown of the starch, leading to moist, sticky crumb. It is difficult to control the desired partial hydrolysis of the starch merely by accurate dosage of this enzyme.

The object therefore exists to break down the starch only to a specified degree of hydrolysis, with the proviso of adequate dosage tolerance for the added enzyme.

In U.S. Pat. No. 4,416,903 it is proposed that the known alpha-amylase derived from fungi be made usable for the purposes of freshness retention by embedding in a sugary medium having a stabilizing effect against thermal stress. The process does not work without added emulsifier and sugar, and it cannot be used for numerous baked articles in which added sugar is undesirable.

PCT application WO 89/08403 also relates to the use of alpha-amylase derived from fungi for keeping bread fresh. Therein there is proposed the use of an acid-stable alpha-amylase derived from fungi which, even at the elevated temperatures of the baking process, is still sufficiently active, or in other words cleaves starch up to a specified degree of hydrolysis, in the slightly acid medium of the dough. The enzyme is isolated from black-spored Aspergillus strains and has a pH optimum of 3 to 5 at 60 to 70° C.

In general, relatively high enzyme dosages must be added to achieve an effect in the uses of alpha-amylases derived from fungi described hereinabove.

U.S. Pat. No. 4,654,216 attempts to solve the problem of keeping bread fresh by means of special specificity of the enzyme used. It relates to a pullulanase, which is used together with amylase derived from bacteria or from malt. Supposedly it cleaves mainly the branched amylopectin and thus supports the action of the amylases. Since the enzymes used are thermally stable, the problem that the enzyme must be added with pinpoint accuracy persists here, and must lead to difficulties in practice.

Another method which is also based on the specificity of the enzyme used is claimed in PCT Application WO 91/04669. Therein maltogenic exoamylases, otherwise known as beta-amylases, are proposed for prevention of staling. This enzyme species cleaves exclusively maltose from starch molecules. Two different beta-amylases derived from bacilli are cited. Their source and preparation are described in European Patent 234858 and U.S. Pat. No. 4,604,355.

Since these enzymes are highly thermally stable—both enzymes still retain more than 50% of their activity after 30 minutes of thermal stress at 80° C.—it can be assumed that their action is not limited in the course of time, or in other words that they act throughout the entire baking process and thereafter. Consequently, at least part of the enzymes must survive the baking process and thus still be present in active condition even in the finished baked article. One of the doctrines of food technology is that if enzymes are present in ready-to-eat products they should be in inactivated condition, which is not assured with certainty in this case and is a disadvantage. The action of these enzymes supposedly comprises quantitatively limited cleavage into lower molecular weight fragments, which improve water-retention capability and simultaneously prevent recrystallization of the residual starch. The reaction goes as far as beta residual dextrin, where it stops. Another disadvantage is that the cleavage products are exclusively sugars, which is undesirable in some cases for flavor reasons.

Thermally stable exoglucanases such as beta-amylases or amyloglucosidases are also proposed in European Patent 412607 for prevention of staling. They can be supplemented or replaced by alpha-1,6-endoglucanases such as pullulanase. Here also the enzymes are active during baking between 80 and 95° C., and their complete inactivation at the end of the baking process is not assured with certainty. Supposedly the amylopectin components in particular are selectively hydrolyzed by the choice of these specificities, and the reaction can also go beyond residual dextrin. Thus the problem of adding enzyme with pinpoint accuracy is also present here.

SUMMARY OF THE INVENTION

Object and Achievement

The object of solving the problem of keeping bread fresh therefore comprises selective partial hydrolysis of the starch by enzymes. The following requirements must additionally be met:
1. High enzyme dosages must not be needed to achieve the effect
2. The enzyme addition must be dosage-tolerant
3. The enzyme must be completely deactivated after the baking process
4. The cleavage products must cause the least possible change in flavor, and in particular they must not consist exclusively of sugar.
5. The bread aroma must be preserved as much as possible.

The object is achieved by using an alpha-amylase which is distinguished from the prior art in terms of origin, specificity and thermal stability. This alpha amylase is produced by *Thermoactinomyces vulgaris*.

DETAILED DESCRIPTION OF THE PREFERRED EMBODIMENTS

Preparation of the Enzyme

Alpha-amylase from *Thermoactinomyces vulgaris* was disclosed in East German Patent DD 288395. Therein there is described the preparation by fermentation of *Thermoactinomyces vulgaris* as well as the use thereof for cleavage of starch with formation of hydrolyzed products rich in maltose and maltotriose. The enzyme has an isoelectric point of 5.57, a pH optimum of between 4 and 6 and relatively low thermal stability. Thus activity is no longer found after the enzyme has been subjected to thermal stress in aqueous solution at 70° C. for 20 minutes. Its cleavage pattern is unusual. It is described in East German Patent DD 287732: In the hydrolysis of native wheat starch, there are obtained soluble products comprising 4.3% glucose, 54.5% maltose and 20.5% maltotriose, with soluble starch fragments as the remainder. Thus one characteristic of the alpha-amylase according to the invention is a content of 50 to 60 wt % of maltose in the soluble cleavage products of the hydrolysis of wheat starch.

The enzyme produced according to the preparation technique of culturing *Thermoactinomyces vulgaris* as described in the cited East German patents can be used directly for the purposes of the present invention, namely in the process for preparation of baked articles with improved freshness retention. In Hansen et al., Int. J. Pept. Protein Res. (1994), 44(3), pp. 245–252, there are described various properties of this enzyme, such as the molecular weight and $K_m$ value. The amino acid sequence is also documented, as is the fact that the proteinase contained in *Thermoactinomyces vulgaris* is capable of cleaving the alpha-amylase into two fragments, both of which are active within the meaning of the invention. It has been found, however, that *Thermoactinomyces vulgaris* is not a particularly productive strain for generation of alpha-amylase. Thus successful experiments on preparing this enzyme by genetic engineering have already been performed. As an example, the paper of Hofemeister et al., Appl. Environ. Microbiol. (1994), 60(9), pp. 3381–3389 describes the isolation of the alpha-amylase gene from *Thermoactinomyces vulgaris,* documents its basic sequence and discusses the expression of the gene into *Escherichia coli* and *Bacillus subtilis. B. subtilis* is a particularly effective host organism. By means of a gene construct containing a *B. subtilis* plasmid as vector, the *Thermoactinomyces vulgaris* gene was incorporated into the host organism. The latter is then cultured in a suitable nutrient medium based on carbon, nitrogen and inorganic salts. Since the enzyme yield is much higher in the genetic engineering preparation technique, this is preferred.

Application of the Enzyme

Compared with the prior art, it was unexpected that an alpha-amylase with the above properties, wherein the aforesaid cleavage pattern during starch hydrolysis lies approximately between that of an alpha-amylase and a beta-amylase, while the thermal stability is so low, would have such striking effects in keeping bread fresh. The effect is independent of the type of baked article.

Baked articles are understood primarily as those prepared using added yeast. Examples are white bread, wheat and rye mixed bread, or whole-grain bread.

The enzyme can be mixed in with the very flour used for making the baked articles. It can also be contained in the baking ingredient which is added to the flour or dough. In many cases, however, it is mixed directly with the dough. In any case it must be present in the dough when the baking process begins. The freshness-retention enzyme according to the invention must be added in a quantity which is effective for prevention of staling. The quantity of enzyme is usually defined in terms of enzyme activity, which can be given, for example, in AZ units. One AZ unit corresponds to the enzyme activity per gram of enzyme preparation which catalyzes the cleavage of a number of glycoside bonds equivalent to 0.75 mmol of oligosaccharide under the given conditions (pH=5, 20° C. 6% solution of soluble starch, as substrate). See also Willstätter, Waldschmidt-Leitz and Hesse, Z. f. physiol. Chem., Vol. 126, page 143, 1922.

The analysis is performed as follows: Into a 50-ml wide-necked flask there is introduced 5.5 ml of 6% starch solution (Merck, Order No. 1252), which has been dissolved almost completely by brief heating and adjusted to pH=5 with sodium acetate buffer. It is thermostatted at 20° C. Thereafter 2 ml of the enzyme solution to be determined is added with swirling, and the reaction mixture is left to stand for exactly 15 minutes at 20° C. At exactly this time the reaction is stopped with 0.5 ml of 1 N hydrochloric acid. Then 10 ml of 0.1 N iodine solution followed immediately by 20 ml of 0.1 N sodium hydroxide solution is added to the reaction mixture. After thorough stirring, the mixture is left to stand for 20 minutes. Then 5.2 ml of 1 N sulfuric acid is added and the mixture is titrated with 0.1 N sodium thiosulfate solution until colorless.

In a parallel experiment, a blank value is determined by replacing the enzyme solution with pure water.

The difference between test and blank values corresponds to the consumption of 0.1 N iodine solution (V) in ml, which is inserted in the calculation of the AZ activity as follows:

$$AZ = \frac{0.0011288 \times V^2 + 0.23736 \times V}{\text{Weight of starting sample in } g} \times 0.96$$

The weight of the starting sample enzyme is chosen such that the value for V lies between 0.8 and 1.5 ml.

Depending on type of flour and the intended baked article, 20 to 20,000 AZ are used per 100 kg of flour, preferably 100 to 10,000 AZ and particularly preferably 300 to 3000 AZ per 100 kg of flour.

The freshness-retaining enzyme according to the invention can be added on its own as the only enzymatic active substance. Obviously, however, it is also possible to add other enzymes such as further alpha-amylases, glucosidases, proteinases, lipases, lipoxygenases, hemicellulases (pentosanases, xylanases), oxidases or transglutaminases. The addition of xylanase with baking activity appears to be particularly effective in this connection. It increases the volume of the baked article particularly effectively and leads to remarkably soft crumb. It is postulated that this enzyme makes part of the insoluble pentosans water-soluble or at least water-swellable, whereupon these constituents can perform the function of water absorption, thereby intensifying the freshness-retaining action of the enzyme according to the invention. Xylanases are added in dosages of 100 to 20000 xylanase units per 100 kg of flour, advantageously together with the alpha-amylase from *Thermoactinomyces vulgaris*. The unit of activity for xylanase is defined as follows: 1 xylanase unit is that quantity of enzyme which liberates 1 µmol of xylose from soluble xylan in 1 minute at 30° C. The xylan substrate is obtained from oat cnaff and, for analysis, is used in 0.25% solution at pH=4,5. The xylose can be determined photometrically, for example with p-hydroxybenzoic acid hydrazide. There is also no need to do without the other usual additives in bread production, such as emulsifiers or preservatives which are known in themselves.

Advantageous Effects

An advantageous freshness-retention effect is observed in the baked articles made by the process according to the invention. For example, white bread can be described as fresh even after four days of storage: The crumb is still soft and succulent, and the crust is not leathery. High enzyme dosages are not necessary to achieve the effect. Furthermore, the dosage tolerance is good: Even with an overdose several times too large, the bread defect of sticky, moist crumb common to thermally stable alpha-amylases derived from bacteria does not develop. The enzyme according to the invention is completely deactivated after the baking process and can no longer be detected in the finished baked article by activity measurement. Although the starch fractions present in the dough have undergone partial hydrolysis, meaning that several low molecular weight, sugar-like reaction products must have been formed, no change of flavor in the form of increased sweetness is observed.

On the whole, the softness of the crumb as well as the flavor and aroma are undeniably preserved during relatively long storage. The *Thermoactinomyces vulgaris* alpha-amylase according to the invention can be advantageously combined with additives common to baking, such as other enzymes and/or baking emulsifiers, water-soluble colloids and preservatives.

EXAMPLES

Performance of Baking Experiments

In a spiral kneader (Kemper brand) there is prepared a dough from 1500 g of flour, 870 ml of water, 45 g of yeast, 30 g of salt and 5 g of ascorbic acid. For this purpose the dough is kneaded for 2 minutes at the lower stage 1 and for 6 minutes at the higher stage 2. Any enzyme addition takes place in the aqueous phase at the beginning of the kneading process. The dough temperature is 26 to 27° C. After the dough has rested for 20 minutes, it is divided into 4 parts weighing 600 g each for making square-loaf white bread, placed in the pan, cooked for 75 minutes at 32° C. and 80% relative humidity and then baked at 230° C. Using a compressimeter, the crumb firmness is determined on the fresh bread after it has cooled, or in other words after about three hours, then after 24 hours and after four days. Lower numbers correspond to softer crumb and thus to better freshness retention.

Description of the Compressimeter Measurement

There is used a compressimeter of the F. Watkins Corporation, West Caldwell, USA. The instrument measures the compressibility of the crumb of the bread. It shows the force in scale divisions needed to indent the crumb to a given depth. A bread slice with 15 mm thickness is placed in the instrument and centered under the indenter. Scale D is set to zero with the right screw. A penetration depth of 3 mm is set for fresh bread and of 1.5 mm for old bread (storage time 1 to 4 days). For the measurement, the motor is turned on in order to push in the indenter by means of thread-operated tension. Once the desired penetration depth indicated on scale D has been reached, the motor is turned off and the applied force is read on scale J. The scale divisions correspond approximately to the weight in grams with which the indenter has indented the crumb. Low numbers correspond to soft crumb and thus also to better freshness retention.

Example 1 to 3

Baking cycles with the following enzyme additions were performed according to the above baking procedure:

Example 1: without enzyme addition (=comparison example)
Example 2: with 1.3 g of *Thermoactinomyces vulgaris* alpha-amylase (TV-A) per 100 kg of flour, with an activity of 785 AZ per gram
Example 3: with 2.6 g of *Thermoactinomyces vulgaris* alpha-amylase (TV-A) per 100 kg of flour, with an activity of 785 AZ per gram The measurement of the freshness-retention effect was performed with the compressimeter in the manner described above.

TABLE 1

Compressimeter measurements

| Example | Additives g/100 kg flour | after 3 hours | after 1 day | after 4 days |
|---|---|---|---|---|
| 1 | without TV-A | 14 | 27 | 28 |
| 2 | with 1.3 g TV-A | 10 | 17 | 23 |
| 3 | with 2.6 g TV-A | 8 | 12 | 16 |

Result

In the case of addition of *Thermoactinomyces vulgaris* alpha-amylase, the better compressibility and thus the greater softness of the crumb is clearly evident even after four days. The starting quantities used, relative to 100 kg of flour, were 1020 AZ in Example 2 and 2040 AZ in Example 3.

What is claimed is:

1. A process for making baked articles, comprising:
   mixing *Thermoactinomyces vulgaris* alpha-amylase with flour, with a dough containing the flour, or with one or more baking ingredients which are added to the flour or to the dough containing the flour, thereby providing a mixture;
   wherein a quantity of said alpha-amylase is 20 to 20,000 AZ activity units per 100 kg of flour; and
   wherein said alpha-amylase yields 50–60% by weight of maltose based on a total weight of soluble cleavage products of a hydrolysis of wheat starch by said alpha-amylase; and
   baking said mixture.

2. The process of claim 1, wherein said alpha-amylase is produced by a host organism which contains the gene of alpha-amylase from *Thermoactinomyces vulgaris*.

3. The process of claim 2, wherein said host organism is a *Bacillus subtilis* strain.

4. The process of claim 1, further comprising:
   mixing at least one baking enzyme selected from the group consisting of a proteinase, an amylase, a hemicellulase, an oxidase, a transglutaminase and mixtures thereof in the dough containing the flour.

5. The process of claim 1, further comprising:
   mixing a xylanase in an amount of 1,000 to 20,000 xylanase units with the dough containing the flour.

6. The process of claim 1, wherein said dough containing the flour further contains an emulsifier.

7. Flour for making baked articles, comprising:
   *Thermoactinomyces vulgaris* alpha-amylase; and flour;
   wherein said alpha-amylase yields 50–60% by weight of maltose based on a total weight of soluble cleavage products of a hydrolysis of wheat starch by alpha-amylase.

8. A baking ingredient for making baked articles, comprising:
   *Thermoactinomyces vulgaris* alpha-amylase, flour and ascorbic acid, wherein said alpha-amylase yields 50–60% by weight of maltose based on a total weight of soluble cleavage products of a hydrolysis of wheat starch by alpha-amylase.

* * * * *